United States Patent
Majeed et al.

(10) Patent No.: US 7,217,546 B1
(45) Date of Patent: May 15, 2007

(54) COMMERCIALLY VIABLE PROCESS FOR HIGH PURITY OF FATTY ALCOHOL $C_{24}$ TO $C_{36}$ AND ITS COSMETIC APPLICATION FOR SKIN HAIR AND NAILS

(75) Inventors: Muhammed Majeed, Piscataway, NJ (US); KalkunteSeshadri Satyan, Bangalore (IN); KanhangadGangadharan Geetha, Bangalore (IN); Tirumale Sharmila, Bangalore (IN); Subbalakshmi Prakash, Piscataway, NJ (US)

(73) Assignee: Sami Labs Ltd, Bangalore (IN)

( * ) Notice: Subject to any disclaimer, the term of this patent is extended or adjusted under 35 U.S.C. 154(b) by 518 days.

(21) Appl. No.: 10/604,203

(22) Filed: Jul. 1, 2003

(51) Int. Cl.
  *C12P 7/04* (2006.01)
  *C12P 7/02* (2006.01)
(52) U.S. Cl. ...................... 435/157; 435/155
(58) Field of Classification Search ................ 435/155, 435/157
  See application file for complete search history.

(56) References Cited

U.S. PATENT DOCUMENTS 5,747,305 A * 5/1998 Jackson ...................... 435/134
5,856,316 A * 1/1999 Laguna Granja et al. ... 514/164
6,586,201 B1 * 7/2003 May et al. ..................... 435/67

OTHER PUBLICATIONS

Jackson et al (JAOCS 73(3):353-356 (1996).*
Gunnlaugsdottir et al (JAOCS 74(11):1483-1490 (1997).*
Gunnlaugsdottir et al (JAOCS 74(11):1491-1494 (1997).*

* cited by examiner

*Primary Examiner*—Leon D. Lankford, Jr.
*Assistant Examiner*—Susan Hanley

(57) ABSTRACT

The present invention discloses an economically viable process for producing large quantity of higher fatty alcohol of chain length $C_{24}$–$C_{36}$ from natural waxes. The said alkanols have enriched percentage of 70–95% of $C_{28}$ fatty alcohol (Octacosanol) along with less percentage of lower chain length fatty alcohols. The invention discloses the use of supercritical carbon dioxide extraction along with immobilized enzyme for saponification. The present invention also discloses the cosmetic applications of alkyalkanols collectively referred to as policosanol, for control of sebum secretion and as anti-acne component effectively used in cosmetic formulations.

1 Claim, No Drawings

COMMERCIALLY VIABLE PROCESS FOR HIGH PURITY OF FATTY ALCOHOL $C_{24}$ TO $C_{36}$ AND ITS COSMETIC APPLICATION FOR SKIN HAIR AND NAILS

BACKGROUND OF INVENTION

1. Field of Invention

This invention discloses a commercially viable process for producing higher fatty alcohols ($C_{24}$–$C_{36}$) using a novel technique of supercritical carbon dioxide extraction that incorporates an immobilized hydrolyzing enzyme, and describes the cosmetic applications of the higher fatty alcohols extracted.

2. Prior Art

The composition of different groups of compounds from different kinds of waxes has been reported. J. A. Lamberton et al, 1959 &, Horn A and Martic J. S. 1957, who described a method for obtaining fatty alcohols from sugarcane cuticular wax based on homogenous saponification with alcoholic potassium hydroxide, followed by extraction of the unsaponifiable material and further molecular distillation.

U.S. Pat. No. 5,856,316 reported another method to isolate the alcohol mixture using a high efficiency, high vacuum column, and extraction with petroleum ether, followed by distillation of petroleum ether, acetylation of remaining product, alumina chromatography, alkaline hydrolysis and crystallization in ethanol. This procedure for obtaining the mixture of higher aliphatic primary alcohols from animal and vegetable wax is based on the alkaline saponification of the fatty esters followed by the supercritical extraction of $CO_2$, pressures ranging from 60–300 kg/cm$^2$ and temperatures between 25°–100° C. According to this procedure it is possible to obtain only 5% of $C_{20}$ to $C_{36}$ alcohol mixtures. The method uses both chemical hydrolysis and extraction to obtain low purity Policosanol.

Yet another method (JP 60 119514) describes the process for recovering primary normal aliphatic higher alcohols proposed a very similar extraction method applied to waxes, but large scale implementation of this process is difficult.

U.S. Pat. No. 5,856,316 describes the process with the saponification process for 2 to 5 hrs, followed by solid-liquid extraction and crystallization. The yield ranges from 30%, while purity ranges from 80 to 98%. However, use of organic solvents is recommended which are difficult to remove in residual amounts.

Fakuda (Chemical abstracts, 106,17,137413 P) describe the use of fatty alcohols in terms of Lipid lowering effects of sugarcane wax in rats.

Sho H et al (1984), studied the effects of sugarcane wax on serum and liver lipids in rats. Treatment reduces both serum and liver cholesterol level. The beneficial effect of mixture of higher primary fatty alcohols and their effect on ADP and collagen induced platelet aggregation in rats was reported. It significantly inhibited ADP and collagen-induced platelet aggregation suggesting that it is an anti-platelet drug.

Granja et al, U.S. Pat. No. 5,663,156 discloses a process for obtaining primary aliphatic alcohols of 22–38 carbon atoms by saponification and extraction using organic solvents from sugarcane wax. They also disclose its use in the treatment of hypercholestremia, platelet aggregation, ischemia, thrombosis and to prevent drug induced gastric ulcer and to improve normal male sexual activity.

US patent application 20020058713A1 discloses the use of high molecular weight primary aliphatic alcohols obtained from natural products consisting of C20–C 34 carbon atoms for pharmaceutical, food stuff and dietary uses. The invention also mentions the use of such alcohols as anti-inflammatory agents.

U.S. Pat. No. 5,948,822 discloses the use of $C_{18}$ to $C_{26}$ fatty alcohols for treatment of hyperproliferative skin disorders. EP0428642B1 discloses the use of such aliphatic alcohols in the treatment of inflammatory and viral skin diseases.

None of the prior art described above disclose the isolation of highly enriched, high purity fatty alcohols form natural sources, nor do they disclose the use of the same in cosmetic preparations for providing topical benefits.

REFERENCES

J. A. Lamberton et al, 1959, Australian Journal of Chemistry 13, 261 268

Horn A and Martic J. S. 1957, Journal of Science Food and Agriculture 10, 571

Granja et al. U.S. Pat. No. 5,856,316, 1999

Granja et al U.S. Pat. No. 5,663,156, 1997.

Inada S, Furukawa K, Masui T, Honda K, Ogasawara J and Tsubikamoto G, JP 60 119514, 1986

Arruzazabala et al 1993, Prostaglandins Leukot. Essent. Fatty Acids, 49(3), 695–7

Arruzazabala et al 1993, Throm. Res. 69(3) 321–7

Sho H, Chinen I, Fukuda N., 1984, J Nutr Sci Vitaminol (Tokyo) 30(6):553–9

SUMMARY OF INVENTION

One of the main objectives of this invention is to develop an economically viable process without using solvents (especially chlorinated solvents) for extraction and purification purposes. Yet another novelty of the invention is the coupling of the hydrolyzing immobilized enzyme lipase for saponification in the supercritical extraction process itself.

By use of this two step unique process we have overcome the other prior art to obtain high purity Octacosanol without using corrosive and restricted solvents. Further we have reduced multiple steps for getting a desirable percentage of Policosanol. This unique process is economically viable process and it can be used to obtain fatty alcohols from other sources as well.

DETAILED DESCRIPTION

Policosanol is a natural mixture of higher aliphatic primary alcohols (C24–C36) isolated from sugarcane wax and beeswax. It contains 1-Octacosanol, Triacontanol, Tetracosanol, Hexacosanol, Heptacosanol. These $C_{24}$ to $C_{36}$ primary alcohols are also found in sugarcane wax, rice bran wax, beeswax and various vegetable wax. The structures of these primary alkanols are shown below:

| | | |
|---|---|---|
| $C_{24}$ | Tetracosanol | $CH_3(CH_2)_{22}CH_2OH$ |
| $C_{26}$ | Hexacosanol | $CH_3(CH_2)_{24}CH_2OH$ |
| $C_{28}$ | Octacosanol | $CH_3(CH_2)_{26}CH_2OH$ |
| $C_{30}$ | Triacontanol | $CH_3(CH_2)_{28}CH_2OH$ |
| $C_{36}$ | Tetratriacontanol | $CH_3(CH_2)_{32}CH_2OH$ |
| $C_{27}$ | Heptacosanol | $CH_3(CH_2)_{25}CH_2OH$ |

Prior art teaches us isolation of higher fatty alcohol from sugarcane wax by solvent extraction, saponification using alkali and supercritical carbon dioxide extraction. However, for purification to higher levels use of number of chlorinated solvents is recommended.

The lipids in the sugarcane bagasse extracted by conventional solvent extraction methods have the disadvantages of low yields, high manufacturing costs and undesirable sensory properties.

We have developed commercially viable process for obtaining high purity Octacosanol along with other fatty alcohols by incorporating immobilized lipase enzyme in supercritical fluid extraction and use of alcohol to further purify to desired levels.

By incorporating lipase enzyme in supercritical fluid extraction of juice removed sugarcane waste, we have unexpectedly found that we can selectively isolate 60 70% of Octacosanol and 15–20% of other fatty alcohol directly. We are further crystallizing with ethyl alcohol to get higher and desirable percentage of Octacosanol and other fatty alcohol. The incorporation of lipase enzyme in supercritical fluid extraction for production of high purity of Policosanol has not been disclosed yet and therefore novel.

The present invention relates to a process in which sugarcane pressmud and immobilized Lipase enzyme were mixed together and extraction performed with SCFE.

The process involved in this invention is described in detail in the following examples.

EXAMPLE 1

50 kg of sugarcane pressmud (filtered insolubles from sugarcane juice) along with 100 g of immobilized lipase were charged together into extractor for $CO_2$ extraction. The extraction was done with liquid $CO_2$ at 35° C. for 1 to 2 hrs at 200 bar pressure. The extract was separated at RT from $CO_2$. Yield obtained was 3%. 3 kg was crystallized with ethyl alcohol. After crystallization, 2.5% of mixture of fatty alcohols Tetracosanol, Hexacosanol, Heptacosanol, Octacosanol, Triacontanol with total purity of 91% was obtained.

EXAMPLE 2

50 kg of sugarcane pressmud and 250 g of immobilized lipase were mixed together and charged into extractor for $CO_2$ extraction. The $CO_2$ extraction was performed at varied temperature of 35 45° C. under the constant pressure of 220 bar. The extract was separated at RT. Extract was crystallized with ethyl alcohol. The yield and percentage composition was similar to that in Example 1.

Evaluation of Policosanol on sebum levels in human volunteers Study Methodology and Administration Sixteen healthy males of between 18 and 25 years of age were included in the study after they had signed the informed consent form. The main inclusion criterion was those with oily skin (scores >4 on a 0–5 scale). All the subjects were required to abstain from taking drugs, applying cosmetic products to their skin and exposing themselves to sunlight or any other source of ultraviolet radiation throughout the duration of the study.

2% or 5% Policosanol colloidal solution in 1,2 hexanediol was applied (0.2 ml) for seven days, twice daily, on the forehead. One side of forehead being treatment and the other side being the control (1,2 hexanediol treatment).

The efficacy was evaluated based on self-assessment and on the assessment of a panel of five independent cosmetologists, visually, using Sebutape (CuDerm Corp., Dallas, Tex.). The sebutape is made of microporous, hydrophobic polymeric film composed of many tiny air cavities. The surface of the film is coated with a lipid porous adhesive layer that enables the tape to adhere to the skin surface. The tape is applied to the skin test site for optimal period of 1 hr. Sebum is absorbed into the tape, displacing the air in the microcavities. As this occurs, the lipid-filled cavities become transparent to light. Through this process, the sebum output from each follicle forms a sharply defined clear spot, its size roughly corresponding to the sebum volume. When the sebutape are placed on the black background of the score card, the sebum on the tape becomes clearly visible as black spots. These spots are scored by a panel of cosmetologists on a scale of 0–5. These are pooled and from the mean of the scores, the percentage change is calculated from the control treatment site.

The safety and adverse events like erythema, burning sensation, itching, urticaria, edema, dermatitis, ochronosis, dryness of skin and any other non specific reactions, if any, were monitored.

The Policosanol colloidal solution was applied twice a day on one side of the forehead area for seven days. Pre-cleansing with soap/water was done before applications. The following observations were made (i) 2% and 5% Policosanol colloidal solution was found to be safe for local application. It did not show any significant side effects and is safe for use on skin (ii) Topical application of the Policosanol colloidal solution was found to decrease the sebum secretion in a concentration dependent manner. The 2% Policosanol solution reduced the sebum levels by about 11%, while 5% solution reduced sebum secretion by 27%.

(iii) Both self-assessment and assessment by the panel of cosmetologists revealed that 100% of the subjects showed marked decrease in sebum release.

(iv) The colloidal solution was found to be effective in people with moderately high oily skin (scores >3.5).

(v) Additionally, one surprising observation was that Policosanol treatment protected the 1,2 Hexanediol induced dryness of skin and made the skin smooth and soft.

TABLE 1

Effect of Policosanol on the sebum secretion in human volunteers

| Groups | Sebum secretion (Mean Scores of sebutape by a five member panel) | Percentage reduction of sebum release |
| --- | --- | --- |
| Control | 4.2 ± 0.49 | — |
| 2% Policosanol (n = 8) | 3.71 ± 0.41 | 11.6% |
| 5% Policosanol (n = 8) | 3.29 ± 0.33 | 27.66% |

Antimicrobial study against *Propionibacterium acnes* To carry out the antibacterial activity of the products against *P. acnes*, the organism was first cultured in the anaerobic environment for which the anaerobic chamber was used. To standardize the growth of anaerobic culture of *P. acnes* in the anaerobic chamber, different culture media were used.

The anaerobic chamber [Model 8301-230, 3 ft polymer] used in the study purchased from COY LABORATORY, USA, was provided with an automatic Aar lock purge system. The anaerobic condition in the chamber was maintained by initialization with $N_2$ gas and then the mixture of gases of $N_2+H_2+CO_2$ in the proportion 80+10+10. TA to gas tank arrangement was made wherein only $N_2$ was connected to the transfer chamber and mixed gas to the main chamber using Gassing Manifold (Hrishi Biotech, Pune, India)

Preparation of Anaerobic Media The anaerobic media were prepared by heating the media while passing the mixture of gases of $N_2$ and $CO_2$ in 4:1 proportion simultaneously. The media were added with a redox indicator [resazurin: 0.001%] which is colorless in the presence of anaerobiasis and shows blue color in its absence. It was dispensed to 30/20/10 ml vials, sealed with rubber and aluminum clamps and sterilized by autoclaving at 121° C. for minutes.

Antimicrobial Study Preparation of the inoculum: The culture used in the study is *Propionibacterium acnes* ATCC 11827. The culture from the broth was inoculated to the fresh medium in vials (10%) and incubated for 48 hours at 37° C. The optical density (OD) of the culture at 625 nm was measured. It was maintained between 0.64 and 0.80 which corresponds to approximately $12 \times 10^6$ cells/ml [4.0 MC Farland standard]

Procedure: Medium used for this study was reinforced clostridial agar (RCA). The medium that was prepared and sterilized in 30-ml vials was poured into the plates inside the chamber and allowed to solidify. The culture was inoculated [0.3 ml/plate] into the plates and spread. After 30 minutes, antibacterial sterile discs [6 mm] were dispensed (2/plate). 2.5, 5.0, 7.5 and 10 µl of the prepared samples and controls were dispensed onto the discs. The plates were incubated inside the anaerobic chamber at 37° C. for 48 hours duration. Policosanol in different concentrations (0.1–2%) prepared in 1,2 Hexanediol was used as vehicle for the study with 1,2 Hexanediol as control. Clindac A (Clindamycin Phosphate Gel 1% w/w) was used as positive control. The clearance zone formed around the discs were measured and expressed in mm. The results of the study are given below

TABLE 2

Efficacy of Policosanol in inhibiting the growth of Propionibacterium acnes

| Sl. No. | Conc. of the sample (%) | Zone of inhibition (in mm) | |
| --- | --- | --- | --- |
| | | Policosanol | Clindamycin |
| 1 | 2.0 | 12.0 | 11.0 |
| 2 | 1.5 | 9.0 | 9.0 |
| 3 | 1.0 | 8.0 | 8.0 |
| 4 | 0.5 | 0.0 | 0.0 |
| 5 | 0.01 | 0.0 | 0.0 |

As seen in the results above, Policosanol effectively inhibits *Propionibacterium acnes* in concentrations above 1% and the activity is comparable with Clindamycin gel. Inhibition of anaerobic organisms coupled with decrease in sebum secretion complements to its use in cosmetic formulations to control acne, as anti-seborrhea and antimicrobial, additionally could provide moisturizing properties. Policosanol could be used alone or in combination with other antibacterial, blemish erasers, sunscreen boosters amongs thers.

Cosmetic Formulations based on Policosanol are described in the following examples:

EXAMPLE 3

Sebum Control Anti-Acne Cream

| | Percentage |
| --- | --- |
| Actives | |
| Boswellin CG | 0.2 |
| Policosanol | 1.0 |
| Coleus oil | 2.0 |
| Vit E | 1.0 |
| THP | 0.1 |
| Passives | |
| Cetyl Alcohol | 4.0 |
| Glyceryl monostearate | 3.0 |
| Cetostearyl alcohol | 3.0 |
| Isopropyl myristate | 2.0 |
| Myristyl myristate | 1.0 |
| Light liquid paraffin | 5.0 |
| Cetyl palmitate | 1.0 |
| BHT | 1.0 |
| BHA | 0.5 |
| CM-1000 | 2.0 |
| Glycerin | 2.0 |
| EDTA tetra sodium | 0.02 |
| DM Water | 71.0 |
| MPS | 0.2 |
| PPS | 0.02 |
| Imidurea | 0.15 |

(THP is Tetrahydropiperine derived from black pepper fruit, which functions as topical permeation enhancer)

EXAMPLE 4

Sebum Control Sunscreen Cream

| | Percentage |
| --- | --- |
| Actives | |
| Tetrahydrocurcuminoids | 0.2 |
| Vit E | 0.5 |
| Policosanol | 1.5 |
| Ethyl P-methoxy cinnamate | 5.0 |
| Avobenzone | 2.0 |
| Passives | |
| Cetyl Alcohol | 2.0 |
| Glyceryl monostearate | 3.0 |
| Cetostearyl alcohol | 1.0 |
| Isopropyl myristate | 2.0 |
| Spermaceti wax | 2.0 |
| Myristyl myristate | 2.0 |
| Stearic acid | 5.0 |
| PGDCC | 1.5 |
| Olive oil/Almond oil | 1.0 |
| Cetyl Palmitate | 1.0 |
| BHT | 0.2 |
| BHA | 0.02 |
| Glycerin | 3.0 |
| EDTA tetra sodium | 0.02 |
| DM Water | 67.0 |
| Xylosin | 0.6 |
| MPS | 0.2 |
| PPS | 0.02 |
| Imidurea | 0.15 |

EXAMPLE 5

Sebum Control Moisturizing Complex

|  | Percentage |
|---|---|
| Actives | |
| Xyloglucan | 0.15 |
| Umbelliferin | 2.0 |
| Vit E | 1.0 |
| Policosanol | 1.5 |
| Almond Oil | 1.0 |
| Passives | |
| Cetyl Alcohol | 4.0 |
| Spermaceti Wax | 4.0 |
| Squalene | 3.0 |
| Isopropyl myristate | 3.0 |
| Myristyl myristate | 3.0 |
| Stearyl Stearate | 1.0 |
| Cetyl palmitate | 1.0 |
| BHT | 1.0 |
| BHA | 0.01 |
| Glyceryl Mono Stearate | 4.0 |
| MCT Oil | 2.0 |
| Glycerin | 3.0 |
| Carbopol | 0.18 |
| EDTA tetra sodium | 0.02 |
| DM Water | QS |
| MPS | 0.2 |
| PPS | 0.01 |
| Imid Urea | 0.15 |
| Sodium Alginate | 0.13 |
| Perfume | 0.40 |

EXAMPLE 6

Anti-Dandruff, Anti-Seborrhic, Hair Oil

|  | Percentage |
|---|---|
| Actives | |
| Brahmi (oil extract) | 6.63 |
| Neem oil limonoids | 0.15 |
| Vit E | 0.2 |
| Policosanol | 0.5 |
| Rosmarinic acid (98%) | 0.35 |
| Passives | |
| Lauriforte ® (Lauric acid ester fraction from coconut oil) | 3.0 |
| Medium chain triglycerides | 10.0 |
| Isopropyl myristate | 79.0 |
| BHT | 0.05 |
| Perfume | 0.3 |

The invention claimed is:

1. A method of preparing a policosanol composition containing 70% to 95% of $C_{24}$–$C_{36}$ alkanols comprising:
   (i) 75% to 90% (w/w) of 1-octacosanol; and
   (ii) 5% to 15% (w/w) of a mixture of 1-tetracosanol, 1-hexacosanol, 1-heptacosanol, 1-triacontanol, and 1-tetratriacontanol;

comprising the steps:
   (a) mixing a policosanol-containing starting material selected from the group consisting of sugarcane wax, beeswax, and rice bran with an immobilized lipase enzyme to form a mixture,
   (b) extracting the mixture in (a) with supercritical carbon dioxide; and
   (c) isolating said policosanol composition.

\* \* \* \* \*